United States Patent
Morino et al.

(10) Patent No.: US 9,637,435 B1
(45) Date of Patent: May 2, 2017

(54) METHOD FOR PRODUCING HEXAFLUOROISOPROPANOL AND FLUOROMETHYL HEXAFLUOROISOPROPYL ETHER (SEVOFLURANE)

(71) Applicant: Central Glass Company, Limited, Ube-shi, Yamaguchi (JP)

(72) Inventors: Yuzuru Morino, Kawasaki (JP); Shigeru Fujii, Ube (JP); Toshihiro Nakamichi, Ube (JP); Shinya Akiba, Kawagoe (JP); Masaaki Takeda, Kawagoe (JP); Masaki Fujiwara, Tokyo (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 15/363,749

(22) Filed: Nov. 29, 2016

(30) Foreign Application Priority Data

Nov. 16, 2016 (JP) .................................. 2016-223593

(51) Int. Cl.
| | | |
|---|---|---|
| *C07C 41/09* | (2006.01) | |
| *C07C 45/82* | (2006.01) | |
| *B01J 23/44* | (2006.01) | |
| *B01J 21/04* | (2006.01) | |
| *C07C 29/145* | (2006.01) | |
| *B01J 23/46* | (2006.01) | |
| *G01N 30/68* | (2006.01) | |
| *C07C 43/12* | (2006.01) | |
| *G01N 30/02* | (2006.01) | |

(52) U.S. Cl.
CPC ............... *C07C 41/09* (2013.01); *B01J 21/04* (2013.01); *B01J 23/44* (2013.01); *B01J 23/462* (2013.01); *C07C 29/145* (2013.01); *C07C 45/82* (2013.01); *G01N 30/68* (2013.01); *G01N 2030/025* (2013.01)

(58) Field of Classification Search
None
See application file for complete search history.

(56) References Cited

U.S. PATENT DOCUMENTS

| | | | |
|---|---|---|---|
| 3,213,134 A | 10/1965 | Morin | |
| 3,321,515 A | 5/1967 | Moore | |
| 3,418,337 A | 12/1968 | Middleton | |
| 3,468,964 A | 9/1969 | Swamer | |
| 3,490,739 A * | 1/1970 | Buckman | ................ C07C 17/38 |
| | | | 203/52 |
| 3,544,633 A * | 12/1970 | Karsay | .................... C07C 45/85 |
| | | | 568/411 |
| 3,702,872 A | 11/1972 | Regan | |
| 4,250,334 A | 2/1981 | Coon et al. | |
| 4,467,124 A | 8/1984 | Kawai et al. | |

FOREIGN PATENT DOCUMENTS

| | | | |
|---|---|---|---|
| GB | 976316 A | 11/1964 | |
| GB | 2138811 A * | 10/1984 | ............ C07C 45/78 |
| JP | 56-139436 A | 10/1981 | |
| JP | 57-81424 A | 5/1982 | |
| JP | 59-204142 A | 11/1984 | |
| JP | 1-301631 A | 12/1989 | |
| JP | 6-184025 A | 7/1994 | |
| JP | 6-184026 A | 7/1994 | |
| JP | H06184025 A * | 7/1994 | ............. B01J 23/46 |
| JP | 2009-51798 A | 3/2009 | |
| JP | 2009051798 A * | 3/2009 | ........... C07C 29/145 |

* cited by examiner

*Primary Examiner* — Rosalynd Keys

(74) *Attorney, Agent, or Firm* — Crowell & Moring LLP

(57) ABSTRACT

Disclosed is a method for producing a hexafluoroisopropanol, including the steps of (a) purifying a mixture containing hexafluoroacetone and at least 1,1,1-trifluoro-2,2-dichloroethane as an impurity, thereby obtaining a purified hexafluoroacetone containing 120 ppm or lower of the 1,1,1-trifluoro-2,2-dichloroethane; and (b) bringing hydrogen ($H_2$) into contact with the purified hexafluoroacetone in the presence of a catalyst, thereby hydrogenating the hexafluoroacetone into the hexafluoroisopropanol. It is possible by this method to produce the hexafluoroisopropanol with a short reaction time and a high conversion. Therefore, it is possible to particularly advantageously produce fluoromethyl hexafluoroisopropyl ether (sevoflurane) by using the hexafluoroisopropanol produced by the method.

12 Claims, No Drawings

METHOD FOR PRODUCING HEXAFLUOROISOPROPANOL AND FLUOROMETHYL HEXAFLUOROISOPROPYL ETHER (SEVOFLURANE)

TECHNICAL FIELD

The present invention relates to a method for producing hexafluoroisopropanol, and fluoromethyl hexafluoroisopropyl ether known as an inhalation anesthetic "sevoflurane".

BACKGROUND OF THE INVENTION

Hexafluoroisopropanol (hereinafter hexafluoroisopropanol may be expressed as "HFIP" in this specification) is produced in large quantities as a solvent showing specific solubility for polymers and as an intermediate for the production of an inhalation anesthetic "sevoflurane". HFIP is generally produced through hydrogenation of hexafluoroacetone (hereinafter this may be expressed as "HFA" in this specification), and various methods have been proposed depending on the combination of the form of the starting material HFA, its reaction mode, the types of the reducing agent and the catalyst, etc.

As a gas-phase method, there are known a method of hydrogenation of HFA with hydrogen ($H_2$) in the presence of an alumina-supported palladium catalyst ($Pd/Al_2O_3$) (Patent Publication 1) or in the presence of an activated carbon-supported palladium catalyst (Pd/C) (Patent Publication 2), and a method of hydrogenation of HFA hydrate in the presence of a nickel catalyst or an alumina-supported palladium catalyst (Patent Publication 3).

Regarding the method for producing HFIP by hydrogen gas in a liquid phase, there are known a method of using HFA hydrate and a method of using HFA anhydride. As the method of using the anhydride, a method of reacting it over a period of 6 hours at 110° C. to 150° C. under a pressure of 20.0 to 90.0 MPa (200 to 900 atmospheres) using platinum oxide as a catalyst (Patent Publication 4) and the like have been reported.

On the other hand, the method of hydrogenating HFA hydrate in a liquid phase includes a method of reacting it over a period of 3.5 hours at 70° C. to 75° C. under a pressure of 0.35 to 0.7 MPa (3.5 to 7 kg/cm$^2$) using palladium/carbon as a catalyst (Patent Publication 5), and a method of reacting it over a period of 6 hours at 100° C. under a pressure of 0.5 MPa (5 kg/cm$^2$) using palladium/$Al_2O_3$ as a catalyst (Patent Publication 6), etc.

As a method using a reducing agent other than hydrogen ($H_2$), there have been reported a method of reducing HFA anhydride, using sodium borohydride as a reducing agent in a methanol solvent, and similarly a method using lithium aluminum hydride, calcium hydride, sodium hydride or the like as a reducing agent in an oxygen-containing solvent such as diethyl ether, methanol, isopropanol, tetrahydrofuran or the like (Patent Publication 4).

According to Patent Publication 7, hydrogenation of HFA hydrate through contact with hydrogen in the presence of a palladium catalyst produces an excessively-hydrogenated product, 1,1,1-trifluoroacetone (TFA), in addition to the target product HFIP. The TFA is said to be difficult to be separated through distillation, since the boiling point thereof is close to that of the target product HFIP. However, Patent Publication 7 reports that, by using "a combined catalyst of palladium and ruthenium" as the hydrogenation catalyst, the target product HFIP can be produced in a sufficient selectivity, that, even when TFA is produced in a small amount, this compound can be readily converted into 1,1,1-trifluoroisopropanol (an easily separable compound, hereinafter this may be abbreviated as TFIP), and that, accordingly, after the reaction, it has become greatly easy to obtain hexafluoroisopropanol having a high purity (see the following).

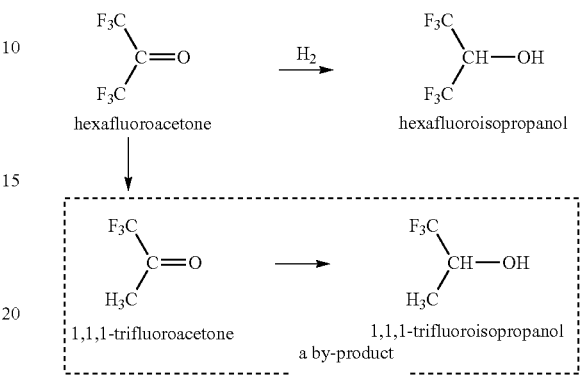

On the other hand, Patent Publication 8 reports that, when a crude HFIP obtained through hydrogenation of HFA in the presence of a catalyst is treated with an organic amine compound, hardly-separable TFA can be removed out of the system in the form of "an associate with the amine compound", and through subsequent distillation, HFIP not substantially containing TFA can be obtained.

Further, it is reported that, when HFA is hydrogenated through contact with hydrogen gas at −20 to 60° C. in the presence of a metal catalyst such as palladium, ruthenium or the like or a catalyst carrying the metal, in a hydrogen fluoride solvent, HFIP not substantially containing excessively-hydrogenated 1,1,1-trifluoroacetone can be obtained (Patent Publication 9).

Regarding the production of hexafluoroacetone (HFA) that is the starting material for producing HFIP, there is known a method of epoxidating hexafluoropropene (Patent Publication 10), followed by isomerizing the resultant epoxy compound in the presence of a catalyst to obtain HFA (Patent Publication 11). There is also known a method of chlorinating acetone to give hexachloroacetone (Patent Publication 12), followed by subjecting the resultant hexachloroacetone to a substitutive fluorination with hydrogen fluoride in the presence of a chromium-supported activated carbon catalyst or the like (Patent Publication 13).

As described above, HFIP is extremely important as a starting material for producing an inhalation anesthetic sevoflurane (chemical name: fluoromethyl-1,1,1,3,3,3-hexafluoroisopropyl ether). Specifically, as illustrated in Patent Publication 14, an inhalation anesthetic sevoflurane can be produced by adding concentrated sulfuric acid and hydrogen fluoride to paraformaldehyde, then heating the resultant mixture at a predetermined temperature and dropwise adding HFIP thereto.

PRIOR ART PUBLICATIONS

Patent Publications
  Patent Publication 1: U.S. Pat. No. 3,468,964
  Patent Publication 2: U.S. Pat. No. 3,702,872
  Patent Publication 3: Japanese Patent Application Publication No. S57-81424
  Patent Publication 4: U.S. Pat. No. 3,418,337

Patent Publication 5: Japanese Patent Application Publication No. S59-204142
Patent Publication 6: Japanese Patent Application Publication No. H1-301631
Patent Publication 7: Japanese Patent Application Publication No. 116-184025
Patent Publication 8: Japanese Patent Application Publication No. 116-184026
Patent Publication 9: Japanese Patent Application Publication No. 2009-051798
Patent Publication 10: U.S. Pat. No. 3,321,515
Patent Publication 11: U.S. Pat. No. 3,213,134
Patent Publication 12: Japanese Patent Application Publication No. S56-139436
Patent Publication 13: Japanese Patent No. S39-13060
Patent Publication 14: U.S. Pat. No. 4,250,334

SUMMARY OF THE INVENTION

According to the methods disclosed in Patent Publications 1 to 3 and 5 to 9, HFIP, which is an important organic intermediate compound, can be mass-produced through a catalytic reaction using HFA as the starting material. The metal catalyst necessary for the hydrogenation reaction contains a noble metal such as palladium, platinum or the like as an active ingredient. Its significant characteristics are that the catalytic activity thereof is high, and even though used in an extremely small amount as compared with the starting material HFA, HFA can be converted into HFIP at a high conversion (in other words, the catalyst turnover is high).

However, the method for producing HFIP through catalytic hydrogenation has an unignorable problem in that "the reaction rate lowers with the progress of reaction". Specifically, within almost 3 hours after the start of hydrogenation of hexafluoroacetone, the reaction rate is high, but thereafter gradually lowers. The reaction does not stop, and any influence is not given to the quality of the product, but the reaction rate lowers disproportionately in and after the middle of the reaction, as compared with that at the start of the reaction. Here, hexafluoroacetone (HFA) is an expensive reagent. Accordingly, it is desired that the hexafluoroacetone conversion through the hydrogenation reaction could reach 80% to 100% (preferably 90% to 100%, especially preferably 98% to 100%). As described above, the reaction rate at around the end of the reaction is extremely slow, and therefore, for attaining such a high reaction conversion, a relatively long reaction time is needed (see Comparative Examples given hereinafter), and some improvement has been desired. (In this specification, "from the middle to the end of the hydrogenation reaction" is, though not always limited thereto, meant to indicate a stage where the HFA conversion has reached around 70% or more from the start of the reaction.)

As described in the section of "Step 4" given hereinafter, in "hydrogenation of HFA", acid components such as hydrogen chloride, hydrogen fluoride and the like are formed with the progress of the reaction, and the pH inside the reaction system gradually lowers. Here, it is understood that, when a small amount of "acid acceptor (basic substance)" has been previously added to the reaction system, the acidic substances to be formed as by-products during the hydrogenation reaction can be immediately neutralized. As a result, the reaction rate is known to significantly increase. (For example see Patent Publication 7. In fact, as shown in Examples to be given hereinafter, when the hydrogenation reaction is carried out with the addition of an acid acceptor, the reaction finishes significantly within a short period of time as compared with a case with no addition of an acid acceptor.) However, even in the "case with the addition of an acid acceptor", the phenomenon that "the reaction rate lowers with the progress of reaction" could not be evaded. Even when the amount of the acid acceptor is increased, the phenomenon could not be sufficiently improved (see Examples and Comparative Examples given hereinafter).

It is an object of the present invention to provide a novel method for producing hexafluoroisopropanol from hexafluoroacetone as the starting material, wherein the reaction rate from the middle to the end of the hydrogenation reaction is prevented from being lowered.

In view of the above-mentioned problems, the present inventors have made an eager study. As a result, the inventors have found that the content of 1,1,1-trifluoro-2,2-dichloroethane ($CF_3CHCl_2$; hereinafter this may be expressed as "HCFC-123") among the impurities contained in hexafluoroacetone at the start of hydrogenation has a close correlation with the "reaction rate in and after the middle of the reaction" of hydrogenation.

Specifically, the present inventors have obtained a surprising finding that, when the hydrogenation reaction is started using hexafluoroacetone in which the concentration of HCFC-123 has been reduced to 120 ppm or less, the above-mentioned "phenomenon of the decrease in the reaction rate with the progress of reaction" can be significantly suppressed. As a result, even though the amount of the hydrogenation catalyst and the amount of the acid acceptor are the same, the hydrogenation reaction can be made to reach the level of a desired reaction conversion within a shorter period of time.

This HCFC-123 is a compound that is recognized in an amount more than 120 ppm, as a by-product in producing HFA through a reaction of hexachloroacetone and hydrogen fluoride. (Immediately after the synthesis of HFA through fluorination of hexachloroacetone, the compound is contained in the reaction mixture in an amount of a few thousand ppm, and as shown hereinafter, the compound is still contained therein in an amount of 1000 ppm to 2000 ppm or so even after its simple distillation.) In general, the starting material acetone does not contain such a compound having "two carbon atoms". Therefore, it is considered that, under a severe condition of chlorination or fluorination, the carbon-carbon bond would be severed to partially produce the "compound having two carbon atoms". (Even when HFA is synthesized by a different process, the process shall necessarily include a chlorination step and a fluorination step, and therefore formation of the by-product HCFC-123 could be assumed.)

HCFC-123 has a boiling point of 28° C., which differs from the boiling points of HFA and HFA trihydrate. However, in a simple distillation of HFA trihydrate, HCFC-123 could not be completely removed from HFA trihydrate (see Reference Examples given hereinafter). In addition, HCFC-123 itself does not have an active functional group reactive with HFA and HFIP. After obtaining HFIP after the hydrogenation, the compound can be sufficiently separated and removed from the HFIP through distillation. Consequently, heretofore, no one has tried an idea of purposely separating and removing HCFC-123 to a high degree from a state of HFA or HFA trihydrate.

The cause and the reason why the presence of HCFC-123 in an amount of more than 120 ppm would prolong the reaction time are not clear. As obvious in Example 1 to be given hereinafter, the peak of "HCFC-123" disappears in a relatively early stage after the start of hydrogenation. On the other hand, the "phenomenon of reaction rate lowering" is recognized to occur considerably later on. From these, a probability may well be taken into consideration that "HCF-123" itself would not directly interfere with the hydrogenation.

In connection with this, in the case where HCFC-123 is contained in HFA and when HCFC-123 is hydrogenated, it may be considered that 1,1,1-trifluoro-2-chloroethane ($CF_3CH_2Cl$; hereinafter this may be expressed as "HCFC-133a" in this specification) would be formed and that, when this is further hydrogenated, 1,1,1-trifluoroethane ($CF_3H_3$) would be formed. Both reactions are accompanied by the production of a by-product hydrogen chloride (HCl).

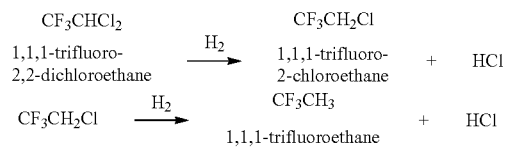

There may be a possibility that the hydrogen chloride formed in this reaction would act as a catalyst poison to lower the activity of the metal catalyst, therefore inducing "prolongation of the reaction time". However, as shown in Examples and Comparative Examples to be given hereinafter, in the case where HCFC-123 exists in an amount of more than 120 ppm and when the reaction is started by increasing the amount of the acid acceptor, the reaction rate is increased generally, but the "phenomenon of reaction rate lowering in and after the middle of reaction" does not disappear. From these, it is presumed that there would be any other factors that could not be clarified by the above-mentioned explanation.

The phenomenon that "reaction rate lowering in and after the middle of reaction" could be prevented by "control of the content of HCFC-123" was recognized irrespective of the presence or absence of an acid acceptor (see Examples and Comparative Examples given hereinafter).

From these, it is considered that the effect of "reducing HCFC-123" in the present invention (prevention of the reaction rate lowering in and after the middle of reaction) would be different from and independent of the effect of "addition of acid acceptor in the hydrogenation reaction" (the overall increase in reaction rate).

With that, the present inventors have found that the hydrogenation in the present invention can be carried out especially favorably only in the case where the two requirements of "addition of an acid acceptor" and "lowering of the content of HCFC-123 to a predetermined amount or less" are satisfied.

Anyhow, the "amount of HCFC-123 at the time of starting hydrogenation" is an important index. When this is controlled to be 120 ppm or less, the reaction rate in and after the middle of the hydrogenation reaction can be prevented from lowering, and such are surprising and useful findings. Based on these findings, the present inventors have succeeded in producing HFIP more economically than ever before.

According to the present invention, it has become possible to synthesize hexafluoroisopropanol within a shorter period of time. Accordingly, by synthesizing sevoflurane using the hexafluoroisopropanol produced in the present invention, the inhalation anesthetic "sevoflurane" is produced dramatically more advantageously than ever before from a comprehensive perspective standpoint. In this point, it may be said that the superiority of the present invention is extremely high.

Specifically, the present invention provides a method for producing hexafluoroisopropanol and sevoflurane, as stated in the following "Invention 1" to "Invention 12".

The steps (a), (b) and (c) of Invention 1 correspond to the after-mentioned Steps 3, 4 and 5, respectively. The steps (m), (n), (o)-(q), (r) and (s) of Invention 12 correspond to the after-mentioned Steps 1, 2, 3a, 4a and 5, respectively.

[Invention 1]

A method for producing a fluoromethyl hexafluoroisopropyl ether (sevoflurane), comprising the steps of:
 (a) purifying a mixture containing hexafluoroacetone and greater than 120 ppm of 1,1,1-trifluoro-2,2-dichloroethane as an impurity, thereby obtaining a purified hexafluoroacetone containing 120 ppm or lower of the 1,1,1-trifluoro-2,2-dichloroethane;
 (b) bringing hydrogen ($H_2$) into contact with the purified hexafluoroacetone in the presence of a catalyst, thereby hydrogenating the hexafluoroacetone into a hexafluoroisopropanol; and
 (c) reacting the hexafluoroisopropanol, formaldehyde, and hydrogen fluoride in the presence of a Lewis acid or a Broensted acid.

[Invention 2]

The method of Invention 1, wherein the step (a) is conducted by a distillation.

[Invention 3]

The method of Invention 1 or 2, the step (a) comprises the steps of:
 (d) bringing water into contact with the mixture containing hexafluoroacetone and greater than 120 ppm of 1,1,1-trifluoro-2,2-dichloroethane as an impurity, thereby converting the hexafluoroacetone contained in the mixture into hexafluoroacetone trihydrate; and
 (e) distilling a mixture obtained by the step (d).

[Invention 4]

The method of Invention 3, wherein the step (e) comprises the steps of:
 (f) supplying the mixture obtained by the step (d) into a rectifying column; and
 (g) conducting the distillation with a number of theoretical plates of from 2 to 50 and a reflux ratio of 0.5-8.0.

[Invention 5]

The method of any one of Inventions 1 to 4, wherein the step (a) comprises the step of:
 (h) conducting a quantitative analysis of the hexafluoroacetone by gas chromatography during the purification to see if the content of the 1,1,1-trifluoro-2,2-dichloroethane in the mixture is 120 ppm or lower.

[Invention 6]

The method of any one of Inventions 1 to 5, wherein the catalyst used in the step (b) is a first catalyst comprising at least one metal selected from the group consisting of palladium, platinum, ruthenium, rhodium, and nickel, or a second catalyst comprising the at least one metal supported on a carrier.

[Invention 7]

The method of any one of Inventions 1 to 5, wherein the catalyst used in the step (b) is at least one selected from the group consisting of a third catalyst comprising palladium and ruthenium that are supported on the same carrier, and a fourth catalyst comprising a mixture of a catalyst containing palladium supported on a carrier and a catalyst containing ruthenium supported on a carrier.

[Invention 8]

The method of any one of Inventions 1 to 7, wherein the hydrogenation of the step (b) is conducted in the presence of an acid acceptor in a reaction system.

[Invention 9]

The method of Invention 8, wherein a carbonate or hydrogencarbonate of an alkali metal and a hydroxide of a metal of group 13 of the periodic table are used together as the acid acceptor in the step (b).

[Invention 10]

The method of any one of Inventions 1 to 9, wherein the mixture containing hexafluoroacetone and greater than 120 ppm of 1,1,1-trifluoro-2,2-dichloroethane as an impurity to be purified by the step (a) is prepared by a method comprising the steps of:
(i) chlorinating acetone by chlorine ($Cl_2$), thereby obtaining a mixture containing hexachloroacetone; and
(j) fluorinating the hexachloroacetone by bringing hydrogen fluoride into contact with the mixture obtained by the step (i), thereby preparing the mixture containing hexafluoroacetone and greater than 120 ppm of 1,1,1-trifluoro-2,2-dichloroethane as an impurity.

[Invention 11]

The method of any one of Inventions 1 to 10, wherein the hexafluoroisopropanol produced by the step (b) is separated by a method comprising the steps of:
(k) separating the catalyst of the step (b) from a reaction mixture obtained by the step (b), thereby obtaining a liquid component; and
(l) distilling the liquid component, thereby separating the hexafluoroisopropanol.

[Invention 12]

A method for producing a fluoromethyl hexafluoroisopropyl ether (sevoflurane), comprising the steps of:
(m) chlorinating acetone by chlorine ($Cl_2$), thereby obtaining a mixture containing hexachloroacetone;
(n) fluorinating the hexachloroacetone by bringing hydrogen fluoride into contact with the mixture obtained by the step (m), thereby preparing a mixture containing hexafluoroacetone and greater than 120 ppm of 1,1,1-trifluoro-2,2-dichloroethane as an impurity;
(o) bringing water into contact with the mixture prepared by the step (n), thereby converting the hexafluoroacetone contained in the mixture into hexafluoroacetone trihydrate;
(p) supplying a mixture obtained by the step (o) into a rectifying column;
(q) conducting a distillation of the mixture obtained by the step (o) in the rectifying column with a number of theoretical plates of from 2 to 50 and a reflux ratio of 0.5-8.0 until the content of the 1,1,1-trifluoro-2,2-dichloroethane in the mixture becomes 120 ppm or lower, thereby obtaining a purified hexafluoroacetone trihydrate containing 120 ppm or lower of the 1,1,1-trifluoro-2,2-dichloroethane;
(r) bringing hydrogen ($H_2$) into contact with the purified hexafluoroacetone trihydrate in the presence of an acid acceptor and in the presence of at least one catalyst selected from the group consisting of a first catalyst comprising palladium and ruthenium that are supported on the same carrier and a second catalyst comprising a mixture of a catalyst containing palladium supported on a carrier and a catalyst containing ruthenium supported on a carrier, thereby producing a hexafluoroisopropanol; and
(s) reacting the hexafluoroisopropanol obtained by the step (r) with formaldehyde and hydrogen fluoride in the presence of a Lewis acid or a Broensted acid, thereby producing the fluoromethyl hexafluoroisopropyl ether (sevoflurane).

Advantageous Effect of the Invention

According to the present invention, the method of producing hexafluoroisopropanol using hexafluoroacetone as the starting material exhibits an effect of preventing the reaction rate from lowering from the middle to the end of the hydrogenation reaction. Accordingly, hexafluoroisopropanol can be synthesized within a shorter period of time. Thus, the present invention exhibits another effect that, when sevoflurane is synthesized using the hexafluoroisopropanol, sevoflurane can be more advantageously produced.

DETAILED DESCRIPTION

Hereinafter, the present invention is described in detail. The range of the present invention is not restricted by these descriptions. Besides the exemplifications given hereinafter, the invention can be suitably changed and modified within a range not detracting from the effect and the spirit of the invention. All the publications cited in this specification, for example, prior art documents, and patent application publications, patent publications and other patent documents are herein incorporated in this specification by reference.

In this specification, hexafluoroacetone hydrate refers to a hydrate with no limitation on the number of water molecules or an aqueous solution thereof, and includes hexafluoroacetone trihydrate. In this specification, hexafluoroacetone trihydrate may be expressed as "HFA.3W".

As disclosed in prior art publications, hexafluoroacetone can be expressed by some chemical species, by itself. For example, in an aqueous solution thereof, the compound exists as "hexafluoroacetone trihydrate".

Hexafluoroacetone has a boiling point of −28° C. (atmospheric pressure), and exists as a vapor (gas) at room temperature and ordinary pressure. For convenience in handling, hexafluoroacetone trihydrate obtained as a constant boiling point composition at 106° C. to 108° C. is used as a starting material in many reactions, or is stored. In the present invention, the expression of "hexafluoroacetone" is used to include hexafluoroacetone hydrate.

For describing the present invention more clearly, the steps relating to the present invention are summarized below.

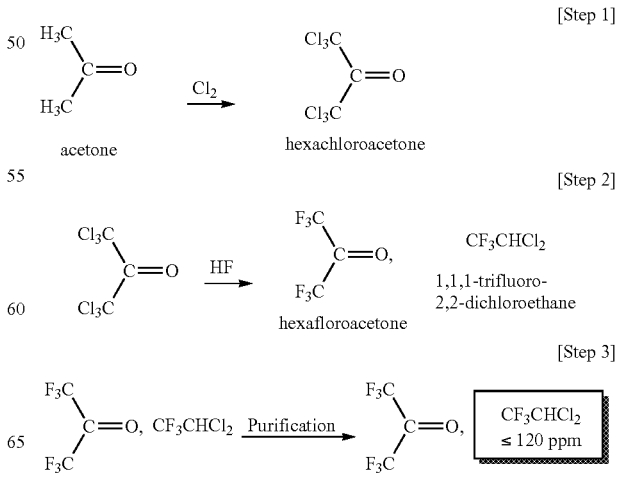

-continued

[Step 4]

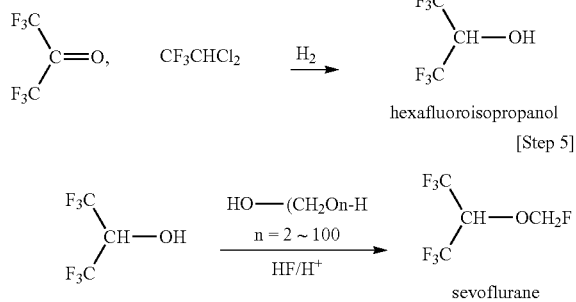

hexafluoroisopropanol

[Step 5]

$$F_3C\diagdown CH-OH \quad \xrightarrow[HF/H^+]{HO-(CH_2On-H \atop n=2\sim100}} \quad F_3C\diagdown CH-OCH_2F$$

sevoflurane

Among the above, Step 3 and Step 4 are indispensable steps of the present invention. According to the present invention, Step 5, or Steps 1 and 2 may be added to these. Of Step 3, one especially preferred embodiment may be expressed as "step 3a". Of Step 4, one especially preferred embodiment may be expressed as "step 4a". The following description includes these.

[Step 1]

Step 1 is a step of chlorinating acetone with chlorine ($Cl_2$) to obtain a mixture containing hexachloroacetone.

This step and the subsequent Step 2 are conventional steps, but are important for understanding the present invention and are described below.

This step is carried out by bringing chlorine (chlorine gas) into contact with acetone. The chlorination in this step is preferably carried out in the presence of a catalyst. As the catalyst, one known as a so-called chlorination catalyst may be used. Concretely, it is possible to use a radical initiator including azo compounds such as azobisisobutyronitrile, azobisvaleronitrile, etc., and peroxides such as benzoyl peroxide, dodecanoyl peroxide, dilauroyl peroxide, t-butylperoxy pivalate, etc., and a phosphorus compound such as red phosphorus, phosphorus pentachloride, phosphorus trichloride, triphenyl phosphine, triphenyl phosphite, etc., a heterocyclic aromatic compound such as pyridine, quinoline, etc., and triethylamine, etc. In addition, the chlorination proceeds through photoirradiation. Among these, a quinoline catalyst is especially preferred.

The amount of the catalyst may be approximately 0.001 to 0.5 equivalents based on the starting material acetone, but can be suitably controlled by a person skilled in the art.

With the progress of chlorination, chloroacetones having one to five chlorine atoms that are partially chlorinated acetones (monochloroacetone, dichloroacetone, etc., in this specification, these may be referred to as "low-order chlorinated compounds") are gradually produced. It is desirable that the reaction is carried out by employing the after-mentioned reaction pressure, reaction temperature and other conditions until all hydrogen atoms of acetone are replaced with chlorine atoms and by using an analyzing means of gas chromatography or the like to check the progress of the acetone conversion and the chlorination degree during the reaction. "Chlorination degree" as referred to herein indicates a mean value of the chlorine atoms introduced per one molecule of acetone, as calculated from the composition of the reaction mixture at a certain time.

Specifically, relative to one molecule of acetone, the necessary theoretical molar number of chlorine ($Cl_2$) for replacing all of the hydrogen atoms of acetone with chlorine atoms (that is, for converting acetone into hexachloroacetone) is "6". Accordingly, by continuing chlorination while the temperature is kept to fall within a range of approximately 20° C. to 260° C. while monitoring the degree of chlorination by gas chromatography, low-order chlorinated compounds could be gradually chlorinated to produce hexachloroacetone at high selectivity.

In this step, excessive chlorine is discharged out of the reaction system while kept unreacted, and therefore can be recovered for reuse.

In general, the reaction pressure preferably falls within a range of 0.05 MPa to 5.0 MPa (absolute pressure—hereinafter the same shall apply in this specification). A range of normal pressure (0.1 MPa) to a slight pressurization of 0.3 MPa or so is simple and preferred. The present invention does not exclude a reaction under a pressure more than 5.0 MPa, but too excessive pressure conditions would put a load on equipment. Therefore, the above-mentioned pressure range is preferred.

The reaction temperature falls generally within a range of 20° C. to 260° C. It is preferably controlled while monitoring the degree of chlorination by gas chromatography. When the reaction temperature is lower than 20° C., it would have some influence on the reaction rate to increase the proportion of low-order chlorinated compounds, and the time for conversion into hexachloroacetone is prolonged. As a result, the productivity may lower. On the other hand, at a temperature higher than 260° C., hexachloroacetone would be vaporized since the boiling point thereof at room temperature/normal pressure is 204° C. This would therefore increase a burden for discharge thereof out of the system. If so, some equipment for preventing the vaporization would be necessary, which is industrially and economically disadvantageous, and employing such a high temperature could provide no advantage.

Regarding the feeding mode for chlorination, any method of a continuous mode or a batch mode is employable with no limitation.

It is only necessary that the reactor is made of a material having heat resistance and corrosion resistance to chlorine, hydrogen chloride, etc. It is possible to use reactors sufficiently durable for the reaction under normal pressure or increased pressure, such as metal containers made of stainless steel, Hastelloy™, Monel™, nickel, platinum or the like, and those lined with tetrafluoroethylene resin, chlorotrifluoroethylene resin, vinylidene fluoride resin, PFA resin, polypropylene resin, polyethylene resin, glass and the like.

The reaction mixture containing hexachloroacetone that is obtained in this step may contain chloroacetones having one to five chlorine atoms, hydrogen chloride, chlorine and others in addition to hexachloroacetone. Therefore, for obtaining hexachloroacetone having a high purity, a purification means of distillation or the like is preferably employed. Prior to distillation, preferably, chlorine and hydrogen chloride are previously separated for reducing the load such as corrosion or the like for the entire apparatus.

According to this method, a high-purity hexachloroacetone can be obtained, and can be used as the starting material in the subsequent fluorination step. Chloroacetones having one to five chlorine atoms that have been separated and recovered as the initial fraction in distillation can be again reused as the starting materials for chlorination.

The distillation apparatus is not particularly limited as long as it is made of a material resistant to chlorine and hydrogen chloride.

[Step 2]

Next, Step 2 is described. Step 2 is a step of fluorinating the mixture containing hexachloroacetone produced in Step 1, with hydrogen fluoride to produce a mixture containing hexafluoroacetone and 1,1,1-trifluoro-2,2-dichloroethane (HCFC-123) that exceeds 120 ppm.

The fluorination includes two modes of a vapor-phase method and a liquid-phase method. As described below, the present reaction favorably proceeds at a relatively high temperature. Therefore, it is preferable to use a vapor-phase method which is easy to carry out at a high temperature.

Preferably, Step 2 is carried out in the presence of a so-called "fluorination catalyst". The fluorination catalyst to be used in this step is an oxide, fluoride, chloride, fluorochloride, oxyfluoride, oxychloride or oxyfluorochloride of a metal. Concretely, the metal is at least one selected from the group consisting of chromium, titanium, aluminum, manganese, nickel, cobalt and zirconium. Aluminum fluoride, aluminum oxide, secondary chromium chloride and the like are especially preferred fluorination catalysts. It is also possible to use a combination of these.

The amount of the catalyst is approximately 0.001 to 0.5 moles or so relative to 1 mol of hexachloroacetone, and can be suitably controlled by a person skilled in the art.

The reaction temperature in the fluorination is 250 to 450° C., preferably 260 to 400° C., more preferably 260 to 350° C. When the temperature is lower than 250° C., the reaction rate of hexachloroacetone may lower. When it is higher than 450° C., excessively fluorinated products may increase, and burden may be put on equipment. Therefore, these two conditions are not preferable.

As the reactor to be used in this step, it is preferable to employ a reactor enough for reaction under normal pressure or increased pressure, such as a metal container made of stainless steel, Monel™, Hastelloy™, nickel or the like, or one lined with tetrafluoroethylene resin, chlorotrifluoroethylene resin, vinylidene fluoride resin, PFA resin, polypropylene resin or polyethylene resin.

In this step, the molar ratio of hydrogen fluoride to hexachloroacetone is stoichiometrically "6", but for efficiently producing hexafluoroacetone at a high conversion and at a high yield, it is desirable to use hydrogen fluoride in an amount more than the stoichiometric amount. Accordingly, the reaction is carried out by using generally 8 moles or more, preferably 10 moles or more, more preferably 12 moles or more of hydrogen fluoride, relative to 1 mol of hexachloroacetone. There is no upper limit in the amount of hydrogen fluoride. Even if it is used in an amount of 50 moles or more, the rate of fluorination could not be increased any more in general. Furthermore, the labor to recover unreacted hydrogen fluoride would increase. Accordingly, using too much of hydrogen fluoride is unfavorable. After the reaction, hydrogen fluoride remaining as unreacted is separated from the organic layer and may be recycled into the reaction system.

The reaction pressure in this step is generally 0.05 to 10 MPa, and is more preferably 0.08 to 1 MPa that is close to normal pressure.

In the case where Step 2 is carried out by a vapor-phase reaction, the contact time of the reaction is generally 1 to 300 seconds, preferably 10 to 60 seconds. However, an optimum contact time may vary depending on the amount of hydrogen fluoride and on the reaction conditions such as the reaction temperature, the catalyst amount, the reaction pressure, etc. Therefore, it may be suitably controlled by a person skilled in the art.

Also in the fluorination step, like in the above-mentioned chlorination step, hexachloroacetone is gradually converted into hexafluoroacetone. Therefore, it is desirable that the reaction is carried out, while monitoring the hexachloroacetone conversion and the progress of fluorination using an analytical means of gas chromatography, etc.

As described above, the reaction mixture obtained in Step 2 contains a by-product HCFC-123 in an amount exceeding 120 ppm (typically several thousand ppm), in addition to the target product HFA. Even after a simple distillation of the mixture, the compound may still remain in HFA in an amount of 1000 ppm to 2000 ppm.

[Step 3]

Next, Step 3 is described. Step 3 is a step for obtaining a "purified hexafluoroacetone" by purifying the "mixture containing hexafluoroacetone and 1,1,1-trifluoro-2,2-dichloroethane in an amount of more than 120 ppm" produced in Step 2, thereby reducing the content of 1,1,1-trifluoro-2,2-dichloroethane contained in the mixture to not more than 120 ppm. The means for purification is not particularly limited, but distillation (precision distillation) is especially preferred.

Hexafluoroacetone produced by the method of Step 2 generally contains hydrogen fluoride and hydrogen chloride as remaining therein. Even HFA after a simple distillation may still contain HCFC-123, which is a problem in the present invention, generally in an amount of 1000 ppm to 2000 ppm, thereby forming a mixture of them. Step 3 is a step for reducing the amount of the HCFC-123 to 120 ppm or less. After this Step 3, the phenomenon "of lowering of the reaction rate in and after the middle of reaction" in the next Step 4 (hydrogenation step) can be noticeably prevented.

As a concrete embodiment of this Step 3, the distillation (precision distillation) operation is preferably carried out after hexafluoroacetone is absorbed by water to convert it into a hydrate thereof (HFA trihydrate having a boiling point of 106° C.), as it is simple and easy to handle.

In producing a hydrate of hexafluoroacetone, the reaction conditions are not particularly limited. Hexafluoroacetone in the form of gas may be mixed into water (water with ice) contained in a reactor so as to be absorbed by water. It is preferable to convert hexafluoroacetone into "hexafluoroacetone trihydrate" that is easy to handle. For this conversion, it is desirable that HFA and water are mixed together so that water could be 3 moles or more relative to 1 mole of HFA. (The molar ratio of water to HFA may be, for example, 3.0:1 to 20:1.)

When more than 3 moles of water is mixed with 1 mole of hexafluoroacetone, a mixture of "hexafluoroacetone trihydrate (boiling point 106° C.)" and "water (boiling point 100° C.)" is obtained. Even when excessive water is added in this operation, it may be removed in the subsequent "distillation operation". Even when excessive water remains, it would not have any influence on the "hydrogenation reaction" in Step 4. On the other hand, when the amount of water is less than 3 moles relative to 1 mole of HFA, a mixture of plural chemical species of "HFA anhydride", "HFA monohydrate" and "HFA trihydrate" that differ in boiling point would be obtained. Such a case is unfavorable, since the subsequent step would be difficult to handle.

Next, "distillation (precision distillation)" especially favorable for the "purification means for reducing HCFC-123 to 120 ppm or less" in Step 3 is described with reference to an example of distilling the above-mentioned "HFA trihydrate".

This "distillation" is an operation of supplying hexafluoroacetone trihydrate into a rectifying column and carrying out a fractional distillation preferably with the number of theoretical plates and the reflux ratio to be described below (in describing the "fractional distillation" here, it may be referred to as "distillation" or "precision distillation" for convenience sake). With this distillation, the amount of HCFC-123 can be efficiently reduced to give "HFA trihydrate in which HCFC-123 is not more than 120 ppm (a purified HFA trihydrate)".

According to this distillation step, HCFC-123, which is a problem in the present invention, can be removed in the form of a fraction from HFA trihydrate, along with "excessively-existing water" of which boiling point is lower than that of "HFA trihydrate". However, as described above, it is not easy to completely separate and remove HCFC-123 from HFA trihydrate. When a too complete removal is tried, some excessive distillation load may be put on the system. As also described above, so far as HCFC-123 could be reduced to 120 ppm or less, the advantageous effect of the present invention (that is, "prevention of reaction rate reduction in and after the middle of reaction" in the hydrogenation in Step 4) could be sufficiently attained. When the amount of HCFC-123 is 110 ppm or less, the effect may be greater. When 60 ppm or less, it is more preferred. When 40 ppm or less, an even more favorable effect may be attained. On the contrary, even when the amount of HCFC-123 could reduce too much, any more effect could not be attained. Accordingly, it is generally unnecessary to reduce "HCFC-123" to, for example, less than 3 ppm, especially less than 1 ppm.

According to the above, as the "purification" in Step 3, a mode of finishing the purification operation at the time when the content of HCFC-123, which is previously targeted at a value falling within a range of, for example, 5 ppm to 110 ppm, has reached the target level could be one of the most reasonable and preferred embodiments. The target level may fall within a range of 10 to 60 ppm, or may fall within a range of 5 to 40 ppm. In consideration of the performance in purification operation (especially distillation), a person skilled in the art may suitably set the target level.

The number of plates of the distillation column may vary depending on the amount of the targeted HCFC-123. It may be, for example, 2 or more and 50 or less. Above all, the number is preferably 3 or more and 30 or less, more preferably 5 or more and 20 or less.

The filler to be filled in the rectifying column may be any of a regular packing or an irregular packing. The regular packing may be any ordinary one, including, for example, Sulzer packing, Mellapak, Techno pack, Flexi pack, etc. The irregular packing may also be any ordinary one, including, for example, Heli pack, Raschig ring, Dixon packing, etc.

The reflux ratio may be 0.5 to 8.0, preferably 0.5 to 7.0, more preferably 0.5 to 6.0.

In the case where HFA trihydrate is used as hexafluoroacetone, this component becomes a bottom component. Therefore, it is preferable that the purification is conducted by distillation or the like while monitoring the amount of HCFC-123 contained in the bottom component through a quantitative analysis by gas chromatography and that the purification operation is continued until the content of HCFC-123 could be confirmed to be reduced to a previously-targeted level of 120 ppm or less.

Regarding the type of the column in carrying out a quantitative analysis through gas chromatography, it is recommended to use a "packed column" prepared by putting an adsorbent solid such as silica gel, activated carbon, zeolite or the like into a column as a column filler, or prepared by putting a solid phase (synthetic silica or the like impregnated with a nonvolatile liquid) into a column. Alternatively, it is recommended to use a "capillary column" prepared by applying a solid phase of an adsorbent or the like to the inner peripheral surface of a hollow capillary of molten silica or the like in a mode of coating or chemical bonding.

In the case where a packed column is used in this step, silica gel, activated carbon or zeolite is preferably used as the column filler. In the case where a capillary column is used, a nonpolar solid phase of polydimethylsiloxane or the like, or a high-polar solid phase of polyethylene glycol or the like is preferably used.

The content of HCFC-123 can be calculated from the "peak area value" to be determined through a quantitative analysis by column chromatography. For example, the component is analyzed by using a gas chromatography apparatus equipped with a flame ionization detector (FID), and the ratio (%) of the peak area of HCFC-123 relative to the total (100%) of the entire peak area is referred to as the content of the compound.

In a quantitative analysis by gas chromatography, an ordinary vapor (nitrogen, argon, hydrogen, helium, etc.) may be used as the mobile phase. The column temperature, the mobile phase gas pressure, the mobile phase flow rate, the column length and others are not particularly limited, and may be suitably controlled by a person skilled in the art.

The description relating to Step 3 made hereinabove indicates a method of precision distillation after conversion (hydration treatment) of HFA into "HFA trihydrate" which is the easiest in handling. However, it should not exclude, from the scope of the present invention, an embodiment where an anhydrous HFA itself with no hydration treatment is subjected to the removal of HCFC-123. In this case, however, a special attention should be paid that anhydrous HFA has a boiling point (−28° C.) lower than that (28° C.) of HCFC-123. In other words, in the case of conducting a separation between anhydrous HFA and HCFC-123 through distillation, the distilled fraction is the target product (anhydrous HFA), and HCFC-123 is concentrated in the bottom. If such low-boiling-point compounds are desired to be separated from each other through distillation, it is necessary to conduct a special operation, such as a distillation under pressurized condition or a distillation under a controlled low-temperature condition. In other words, the embodiment of carrying out Step 3 using anhydrous HFA could not be said to be the most suitable embodiment of the present invention, as putting a large burden on the operation and the equipment.

In the present invention, the most preferred embodiment of Step 3 is referred to as Step 3a. Step 3a is as follows.

[Step 3a]

Step 3a is a step where the mixture obtained in Step 2 is brought into contact with water to thereby convert hexafluoroacetone contained in the mixture into hexafluoroacetone trihydrate, and then the mixture is introduced into a rectifying column and distilled therein at a theoretical stage number of 2 or more and 50 or less and with a reflux ratio of 0.5 to 8.0, and the distillation is continued until the content of 1,1,1-trifluoro-2,2-dichloroethane contained in the mixture can be confirmed to be not more than 120 ppm by gas chromatography, thereby obtaining a purified hexafluoroacetone trihydrate in which the content of 1,1,1-trifluoro-2,2-dichloroethane is 120 ppm or less.

[Step 4]

Next, Step 4 is described. Step 4 is a step of synthesizing hexafluoroisopropanol by hydrogenating the purified hexafluoroacetone obtained in Step 3, through a contact with hydrogen ($H_2$) in the presence of a catalyst.

In the hydrogenation of Step 4, conventional known operation method and condition may be applied directly as they are to carry out the reaction. A unique feature in this step is that HCFC-123 is contained in the starting material HFA only in an amount of 120 ppm or less. With this, however, the reaction rate lowering from the middle to the end of the reaction can be significantly prevented even though the other conditions are completely the same. Consequently, in particular, in the case where the reaction is continued until a high conversion of HFA, the present invention can provide an advantageous effect that the necessary reaction time can be greatly shortened.

In this step, it is preferable to conduct the reaction in a liquid phase by using hexafluoroacetone trihydrate as the raw material, because the reaction may proceed gently and the catalyst activity can be kept high. The above step 3 has been described on the assumption that HFA could also be "anhydrous HFA". In Step 4, however, if the "purified HFA" is anhydrous HFA, it is desirable that the anhydride is converted into the trihydrate by the method described in Step 3, and then the resultant hydrate is hydrogenated in Step 4.

In the following description, the "purified hexafluoroacetone" to be used as the starting material is "HFA trihydrate", and this is reacted in a mode of liquid-phase reaction.

In this step, various catalysts known as so-called "hydrogenation catalysts" are usable as the catalyst. Concretely, "a supported catalyst (also referred to as a heterogeneous catalyst or a solid-phase catalyst)" where at least one metal selected from the group consisting of palladium (Pd), platinum (Pt), ruthenium (Ru), rhodium (Rh) and nickel is supported on a carrier is especially preferred as having a high catalyst activity. A so-called "homogeneous catalyst" where such a metal component is dissolved or dispersed in a suspension state in a liquid phase is also usable, but use of the "supported catalyst" is more preferred. The "supported catalyst", when used, provides another advantage in that the catalyst (solid) can be readily separated for reuse from the reaction mixture (liquid) after the reaction.

As the metal, palladium and ruthenium are especially preferred as the activity thereof is high. The chemical forms of the metal include zero-valence metals, or oxides, hydroxides, chlorides and others, and complexes containing these metals are also usable. Oxidation number of the metal is not limited.

As the carrier, activated carbon and alumina are preferred as they are easy in handling and are easily available.

The supported amount is 0.0001 to 30% by mass, preferably 0.01 to 20% by mass, more preferably 0.1 to 10% by mass, in terms of the supported metal relative to the catalyst mass. Concretely, a commercially-available, palladium-supported activated carbon catalyst where the supported amount is 0.1 to 5% by mass or so, or 0.1 to 5% by mass ruthenium-supported activated carbon catalyst is mentioned as an especially preferred one.

The particle size of the catalyst is not particularly limited. A form suitable for suspending the catalyst is preferred. The use of a fine-powdery catalyst is preferred that facilitates distribution homogenization of the catalyst in a system and enhances contact between the reactants and the catalyst. Fine particles are also preferred for recovering and reusing the catalyst after the reaction and for separating the catalyst from the product. For preparing the catalyst, a known method can be employed. A commercially-available catalyst may be used directly as it is, or after drying or an activation treatment (for example, a treatment of bringing 112 gas into contact with the prepared catalyst at 25 to 200° C.).

The amount of the catalyst is not particularly limited. In general, the amount of the catalyst (total amount of metal component and carrier, or when plural catalysts are used, the total amount thereof) is 0.00001 to 0.1 parts by mass, preferably 0.0005 to 0.03 parts by mass, more preferably 0.001 to 0.01 parts by mass, relative to one part by mass of HFA anhydride.

In this step, the amount (mol % relative to hexafluoroacetone) of the active metal component such as Pd, Ru or the like is a more important factor. However, in this hydrogenation reaction, a complete deactivation of the catalyst hardly occurs. Therefore, the amount of the active metal component is not particularly limited. The amount may be determined by a person skilled in the art in consideration of the desired reaction time. For example, the amount of the metal relative to hexafluoroacetone (when plural species of metals are used, the total thereof) may be set within a range of 0.0001 mol % to 50 mol %, more preferably 0.001 mol % to 1 mol %, even more preferably 0.002 mol % to 0.5 mol %.

As described above, in order that the hydrogenation reaction is carried out without producing a perhydrogenated by-product TFA, it is desirable to use a catalyst containing both palladium and ruthenium as active ingredients. Concretely, it is desirable that the hydrogenation in Step 4 is carried out in the presence of at least one type of catalyst selected from the group consisting of "a catalyst where both palladium and ruthenium are supported on the same carrier" and "a catalyst prepared by mixing together a catalyst including palladium supported on a carrier and a catalyst including ruthenium supported on a carrier". For example, it is one especially preferred embodiment to use a mixture of a Pd/alumina-supported catalyst (or possibly a Pd/activated carbon-supported catalyst) and a Ru/alumina-supported catalyst (or possibly a Ru/activated carbon-supported catalyst) in a manner that the amounts of Pd and Ru are each adjusted to 0.001 mol % to 0.25 mol % relative to HFA" (see Examples to be given hereinafter).

However, the "catalyst type optimization" and the "catalyst amount optimization", and the "HCFC-123 amount" are quite different from and independent of each other. Even when the type and the amount of catalyst are optimized, there may occur a significant difference in the "reaction rate from the middle to the end of reaction" between the case where the amount of HCFC-123 at the start of hydrogenation is more than 120 ppm" and the case where the amount is not more than 120 ppm (this will be exemplified by Examples and Comparative Examples to be given hereinafter).

In this step, previously adding a small amount of "an acid acceptor (basic substance)" to the reaction system and then starting the reaction is preferred, since the reaction rate can significantly increase. It is considered that, with the progress of hydrogenation of HFA, acid components such as hydrogen chloride, hydrogen fluoride and the like (those may be catalyst poisons) increase in the reaction liquid, but the acid acceptor can rapidly neutralize these, and therefore catalyst deactivation would hardly occur and the reaction rate can be thereby increased.

The acid acceptor capable of efficiently reducing chloride ions includes alkali metal carbonates or hydrogencarbonates, alkali metal or alkaline earth metal hydroxides, etc. Of these, alkali metal carbonates or hydrogencarbonates are preferred.

For reducing fluoride ions, it is possible to cite hydroxides, carbonates, hydrogencarbonates and the like of a metal belonging to group 13 of the periodic table.

Specific examples of the alkali metal carbonates and hydrogencarbonates include sodium carbonate, potassium carbonate, lithium carbonate, sodium hydrogencarbonate, potassium hydrogencarbonate, lithium hydrogencarbonate, etc. Specific examples of the alkali metal or alkaline earth metal hydroxides include sodium hydroxide, potassium hydroxide, lithium hydroxide, calcium hydroxide, magnesium hydroxide, etc. Among these, sodium carbonate, potassium carbonate, sodium hydrogencarbonate and potassium hydrogencarbonate are preferred. Sodium hydrogencarbonate is especially preferred.

On the other hand, specific examples of hydroxides, carbonates and hydrogencarbonates of a metal belonging to group 13 of the periodic table include aluminum hydroxide, gallium hydroxide, indium hydroxide, aluminum carbonate, aluminum hydrogencarbonate, gallium carbonate, gallium hydrogencarbonate, etc.

As a method for efficiently reducing fluoride ions, it is also effective to use a complex metal hydroxide such as magnesium aluminate or the like (for example, one shown by a chemical formula "$Mg_xAl_y(OH)_2 \cdot X \cdot nH_2O$" (where X is an anion source, n is a positive integer, and x, y and z each are the number of the ions)). For example, "Halogen Killer (a registered trademark; manufactured by Horyu Co., Ltd.) is commercially available, and its use is simple.

In this step, it is one especially preferred embodiment to use an "alkali metal carbonate or hydrogencarbonate" and a "hydroxide of a metal belonging to group 13 of the periodic table" in combination as the acid acceptor.

The amount of these acid acceptors to be added is not particularly limited. With monitoring the reaction progress, or in accordance with the amount of HCFC-123 contained in the starting material hexafluoroacetone, a person skilled in the art can suitably control the amount of the acid acceptor. Preferably, the amount is within a range of 0.005 moles to 0.1 moles relative to 1 mole of hexafluoroacetone. These can be used singly or in combination. (In the case where plural types of acid acceptors are used, the above-mentioned "addition amount" means the total amount of all the acid acceptors.

Preferably, the acid acceptor is added little by little with stirring to the liquid of hexafluoroacetone trihydrate for uniformly conducting the reaction and for preventing temperature increase owing to heat generation.

As mentioned above, the effect of increasing the reaction rate by "the presence of an acid acceptor" and the "effect of preventing the reaction rate lowering from the middle to the end of reaction" owing to "lowering of HCFC-123" that the present inventors have found are quite different from and independent of each other. Only one of the two could be effective for increasing the reaction rate. However, a combination of the two is more preferred as it is capable of further increasing the reaction rate (see Examples and Comparative Examples to be given hereinafter).

The reaction temperature in this step is generally 80° C. to 110° C., and is especially preferably 85° C. to 105° C.

When the temperature is lower than 80° C., the reaction rate is low. When it is higher than 110° C., some side reactions may occur and the catalyst life may be shortened.

The reaction pressure in this step is 0.05 to 5 MPa, preferably 0.1 to 1 MPa, more preferably 0.1 to 0.5 MPa. When the pressure is less than 0.05 MPa, the reaction rate may be low. On the other hand, when the reaction is carried out under a pressure higher than 5 MPa, the reactor may be constrained.

In this step, the reaction may be carried out using a solvent. The solvent is not particularly limited, so far as it does not react with the starting material and the product in the step. Examples of the solvent include hexafluoroisopropanol, which is the product in the method of the present invention, as well as water, ethers such as diethyl ether, tetrahydrofuran, dioxane, etc., alcohols such as methanol, ethanol, 2-propanol, etc. One alone or two or more of these solvents may be used either singly or as combined.

However, as shown in Examples given hereinafter, in the case where hexafluoroacetone trihydrate is used as the starting material in Step 4, this hexafluoroacetone trihydrate itself is a stable liquid having a high flowability. Therefore, the hydrogenation can sufficiently proceed even when a solvent is not added separately. Consequently, in general, Step 4 can be carried out with no addition of solvent. Even though a solvent is not added, the hydrogenation can proceed. While hexafluoroacetone trihydrate is converted into hexafluoroisopropanol, water molecules of hexafluoroacetone trihydrate are released in the system. As a result, water turns to exist in the system.

Synthesis of hexafluoroisopropanol in this step may be carried out in any mode of batch-wise, semibatch-wise, continuous or flow-system operation. Regarding the material of the apparatus, it is possible to use a metal material such as stainless steel, nickel alloy steel, silver, fluororesin, carbon or polyurethane, or those lined or clad with any of these materials may be used.

Preferably but not indispensably, the reactor is provided with a stirrer. In general, it is desirable that the reactor is provided with a heating unit and/or a cooling unit for temperature control. Especially preferably, the reactor is provided with a cooling unit.

The order of putting the raw materials into a reactor is not limited. It suffices to introduce the above-mentioned hexafluoroacetone and catalyst, then add an alkali metal carbonate or hydrogencarbonate to the reaction system, and then introduce hydrogen gas with stirring to keep the pressure on a predetermined level, and continue the introduction of the hydrogen gas while the temperature is kept to fall within the above range.

The end of the reaction may be confirmed by consumption of a predetermined amount of hydrogen or by termination of the hydrogen absorption. However, as described first, the raw material HFA in this reaction is an extremely expensive reagent. Therefore, it is especially desirable that the reaction is continued until the HFA conversion could reach 98 to 100%. In such a "final stage", a considerable reaction rate lowering is inevitable even under the most excellent condition. In other words, mere apparent "considerable slow hydrogen consumption" could not be any absolute evidence of "reaction completion". Consequently, in carrying out Step 4 on a particularly large scale, it is more preferable that the reaction mixture is timely sampled as needed, and the HFA conversion is monitored through gas chromatography or the like, and that, when the conversion has reached a predetermined level, the reaction is stopped.

After the reaction, the content in the reactor is a reaction mixture containing the target product, hexafluoroisopropanol, and other organic substances and catalyst. A liquid component not containing the catalyst may be taken out of the mixture, and hexafluoroisopropanol may be separated and recovered from the liquid component through distillation.

Separation of the catalyst from the reaction mixture is preferably attained by filtration in the case where the catalyst is the "supported catalyst" that has been described in detail hereinabove. In general, the catalyst can be reused. Therefore, it is efficient and favorable that the catalyst is left in the reactor when the content liquid is transferred from the reactor.

Of Step 4, one especially preferred embodiment is referred to as "step 4a". Its details are as follows.

[Step 4a]

This is a step where the "purified hexafluoroacetone trihydrate" obtained in Step 3a is hydrogenated through contact with hydrogen ($H_2$), in the presence of at least one catalyst selected from the group consisting of "a catalyst carrying palladium and ruthenium supported on the same carrier" and "a catalyst prepared by mixing a catalyst of palladium supported on a carrier and a catalyst of ruthenium supported on a carrier" and in the presence of an alkali metal carbonate or hydrogencarbonate in an amount of 0.005 moles to 0.1 moles relative to 1 mole of the hexafluoroacetone trihydrate, thereby producing hexafluoroisopropanol.

[Step 5]

Next, Step 5 is described. Step 5 is a step of reacting the hexafluoroisopropanol produced in Step 4 with formaldehyde and hydrogen fluoride in the presence of a Broensted acid or a Lewis acid to produce fluoromethyl hexafluoroisopropyl ether (sevoflurane).

Formaldehyde to be used in this step refers to having a concept including equivalents such as paraformaldehyde (formaldehyde polymer, $HO-(CH_2O)_n-H$, n=2 to 100) and trioxane (produced by polymerization of 3 molecules of formaldehyde, 1,3,5-trioxane), etc.

Formaldehyde itself is a vapor (gas) at room temperature and under normal pressure, and is constrained much in handling it, for example, its immediate polymerization in the presence of a small amount of impurities. Accordingly, paraformaldehyde or trioxane that is easy to handle is preferably used. Paraformaldehyde is especially preferred.

The Broensted acid for use in the present invention means a proton (H+) donor, and has an acid dissociation constant (pKa) of approximately 3 or less, preferably 2 or less.

Concretely, the acid includes sulfuric acid, fuming sulfuric acid, nitric acid, anhydrous sulfate, hydrogen bromide, hydrogen iodide, propionic acid, p-toluenesulfonic acid, trichloroacetic acid, tribromoacetic acid, methanesulfonic acid, trifluoroacetic acid, trifluoromethanesulfonic acid, etc. Among these, sulfuric acid, fuming sulfuric acid, anhydrous sulfate, hydrogen bromide, hydrogen iodide, trifluoroacetic acid and trifluoromethanesulfonic acid are preferred. Sulfuric acid, fuming sulfuric acid and trifluoromethanesulfonic acid are more preferred.

The Lewis acid for use in the present invention means an electron pair acceptor, including titanium tetrachloride, phosphorus pentafluoride, boron trifluoride, boron tribromide, antimony pentafluoride, aluminum chloride, boron trifluoride-diethyl ether complex, etc.

Regarding the molar numbers of formaldehyde, hydrogen fluoride, and a Broensted acid or Lewis acid relative to 1 mole of hexafluoroisopropanol, formaldehyde is 0.5 to 2.0 moles, hydrogen fluoride is 3.0 to 12.0 moles, and the Broensted acid or Lewis acid is 0.7 to 3.0 moles. For the purpose of increasing the yield of the target product and for preventing side reactions, it is desirable that the reaction is carried out using 0.78 to 1.65 moles of formaldehyde, 6.05 to 9.50 moles of hydrogen fluoride and 0.90 to 1.74 moles of Broensted acid or Lewis acid.

Among these Broensted acids and Lewis acids, plural types of the acids may be used in combination.

The process for producing fluoromethyl hexafluoroisopropyl ether may be carried out in any mode of batch-wise, semibatch-wise, continuous or flow-type reaction.

As the reactor to be used in this step, it is possible to use reactors enough for reaction under normal pressure or increased pressure, such as metal containers made of stainless steel, Monel™, Hastelloy™, nickel or the like, and those lined with tetrafluoroethylene resin, chlorotrifluoroethylene resin, vinylidene fluoride resin, PFA resin, polypropylene resin or polyethylene resin.

In this step, a reactor equipped with a stirrer may be used, and its use is preferred.

The reaction pressure in this step is approximately within a range of 0.05 to 5.0 MPa. Preferably, the reaction is carried out at around normal pressure that may put no burden on equipment. Specifically, within the above-mentioned pressure range, 0.05 to 2.0 MPa is preferred, and 0.08 to 0.5 MPa is more preferred. Reaction in an open system (that is, at normal pressure) is a preferred embodiment of this step as being especially simple.

The reaction temperature in this step is approximately within a range of 40° C. to 100° C., preferably 50 to 80° C., more preferably 50° C. to 70° C.

In the case where this step is carried out in an open system at normal pressure, it is difficult to greatly increase the reaction temperature to a temperature much higher than the boiling point (57 to 58° C.) of HFIP and sevoflurane, except for the period very nearly at the end of the reaction, since the boiling points of HFIP and sevoflurane at normal pressure are 57 to 58° C. As shown in Examples, of HFIP and sevoflurane, sevoflurane firstly turns into a distillate. Accordingly, in the case where Step 5 is carried out under an open condition at normal pressure, a method is preferred in which the reaction is started from around room temperature, and then the system is gradually heated to maintain a "temperature (within a range of approximately 50 to 60° C. though varying depending on the progress of the reaction) at which sevoflurane is distilled out but HFIP is not", and sevoflurane as a distillate that is formed during the reaction is collected in a trap. At around the end of reaction, the temperature is gradually increased to be higher than this and up to 70 to 75° C. With that, the reaction conversion can be increased further more. Naturally, the reaction temperature setting of such a case can be suitably controlled by a person skilled in the art.

When supplying reaction reagents or immediately after the reaction, some great heat may be generated. Therefore, it is desirable to have a heating unit and/or a cooling unit for temperature control. In particular, it is desirable to have a cooling unit.

The reaction time in this step is generally within a range of 2 to 24 hours. Since it depends on the reaction temperature and the equivalents of the reaction reagents, the time is not always limited to this range. As described above, in the case where the reaction is carried out under an open condition at normal pressure, the reaction may be terminated at the time when evaporation of sevoflurane has stopped. On the other hand, using an analytical apparatus such as nuclear magnetic resonance (NMR), gas chromatography (GC) or the like, the time when the reaction conversion has reached a predetermined level may be considered as the end point of the reaction.

In this step, the resultant fluoromethyl hexafluoroisopropyl ether is preferably purified by using a distillation operation. Specifically, the resultant reaction mixture is washed with water to give a two-layer mixed liquid that contains an aqueous layer containing 1,1,1,3,3,3-hexafluoroisopropanol and an organic layer containing fluoromethyl hexafluoroisopropyl ether. Then, the aqueous layer containing 1,1,1,3,3,3-hexafluoroisopropanol can be separated from the mixed liquid, and the organic layer containing fluoromethyl hexafluoroisopropyl ether can be subjected to a distillation to isolate fluoromethyl hexafluoroisopropyl ether of high purity.

EXAMPLES

The present invention is described in more detail with reference to Examples given hereinafter. However, the present invention is not limited to these. Here, "%" indicating compositional analysis values means "areal %" of the composition obtained by the measurement of a reaction mixture through direct gas chromatography (unless otherwise specifically indicated, the detector is FID). In Examples and Tables given hereinafter, "HCFC-123" represents "1,1,1-trifluoro-2,2-dichloroethane ($CF_3CHCl_2$)", "TFIP" represents "1,1,1-trifluoroisopropanol", "HFA" represents "hexafluoroacetone", "HFIP" represents "hexafluoroisopropanol", "TeFIP" represents "tetrafluoroisopropanol", and "PFIP" represents "pentafluoroisopropanol".

[Preparation Example] Production of Hexafluoroacetone Trihydrate 300 g (5.17 mol) of acetone and 1.85 g (0.01431 mol) of quinolone were put into a 1-$dm^3$ GL (glass lining) reactor equipped with a jacket. While 2262 g (31.90 mol) of chlorine gas was gradually blown thereinto, the reactor was gradually heated up to 185° C., and then stirred as such for a few hours. The resultant reaction liquid was distilled to give 1268 g (4.79 mol) of hexachloroacetone (purity 99.5%; chlorination reaction yield 92.6%; in addition to the acetone, a small amount of pentachloroacetone was detected, but the reaction liquid was directly used in the next fluorination step).

Subsequently, a chromium(III) oxide ($Cr_2O_3$) catalyst was put into a stainless steel reactor equipped with a jacket. 1268 g (4.79 mol) of the hexachloroacetone obtained in the above and 1013 g (50.65 mol) of anhydrous hydrofluoric acid were introduced thereinto by spending 40 hours to conduct a fluorination at 360° C. The obtained crude hexafluoroacetone was absorbed into water, thereby obtaining 959 g (4.36 mol) of a crude hexafluoroacetone trihydrate (fluorination reaction yield: 91.0%). At this time, the content of HCFC-123 in the crude hexafluoroacetone trihydrate was 3550 ppm.

The crude hexafluoroacetone trihydrate produced in this Preparation Example was used as the starting material in Examples and Comparative Examples to be described hereinafter. Therefore, this synthesis was carried out several times.

Next, the crude hexafluoroacetone trihydrate thus obtained as above was subjected to a simple distillation and a precision distillation. Regarding the condition of the precision distillation, the theoretical number of plates was 10 and the reflux ratio was 0.2 to 5.0 in order to see the influence of HCFC-123 contained in the crude hexafluoroacetone trihydrate on the reaction rate in the hydrogenation reaction. As shown in Examples and Comparative Examples, the distillation operation was continued along with a quantitative analysis through gas chromatography until the amount of HCFC-123 was confirmed to be reduced to a previously determined target level, thereby producing "hexafluoroacetone trihydrate containing a predetermined amount (7 ppm to 198 ppm) of HCFC-123".

The reflux ratio in the precision distillation and the HCFC-123 content in Examples and Comparative Examples are shown in the following Table 1.

TABLE 1

|  | Theoretical Number of Plates | Reflux Ratio (reflux amount/distillate amount) | Content of HCFC-123 (ppm) |
| --- | --- | --- | --- |
| Example 1 | 10 | 0.6 | 119 |
| Example 2 | 10 | 5.0 | 7 |
| Example 3 | 10 | 4.5 | 12 |
| Example 4 | 10 | 4.5 | 12 |
| Example 5 | 10 | 2.0 | 52 |
| Example 6 | 10 | 2.5 | 46 |
| Example 7 | 10 | 0.8 | 106 |
| Example 8 | 10 | 0.8 | 106 |
| Comparative Example 1 | 10 | 0.3 | 144 |
| Comparative Example 2 | 10 | 0.4 | 130 |
| Comparative Example 3 | 10 | 0.2 | 198 |

These were used as the starting materials in synthesis of hexafluoroisopropanol.

Example 1

4.1 kg (18.63 mol) of hexafluoroacetone hydrate (trihydrate) [the composition of the hydrate and other impurities are shown in Table 2 below—the content of HCFC-123 before the start of the reaction is 119 ppm] was put into a 5-$dm^3$ stainless steel (SUS-316) autoclave equipped with a stirrer. 0.195% by mass (% by mass relative to HFA hydrate—the same shall apply hereinafter) of 5%-Pd/alumina-supported catalyst (8 g), 0.122% by mass of 5%-Ru/alumina-supported catalyst (5 g), 0.122% by mass of aluminum hydroxide (5 g), and 0.0146% by mass of sodium hydrogencarbonate (0.6 g) were added thereto. The reactor was purged with hydrogen. Stirring was started with heating up to 95° C. with hot water, while the hydrogen pressure was kept at 0.7 MPa. With this, hydrogen absorption began.

After 12 hours, the reaction liquid was analyzed. With this, the HFA hydrate conversion was found to be 95.46%. Regarding the GC purity of HFIP was 94.76%, TFIP was 0.6275% and HFA was 4.54%.

Subsequently, the reaction was continued while the reaction liquid was analyzed. 18 hours after the start of the reaction, the GC purity of HFA reached 0.95% (the HFA hydrate conversion was 99.05%). Therefore, the heating and stirring were stopped to terminate the reaction. At that time, the GC purity of HFIP was 98.23%, TFIP was 0.7544%, and HFA was 0.95%. In Examples 1 and 2 and Comparative Example 1, the reaction was carried out under the same condition except the amount of HCFC-123, and, at the time when the "HFA reaction conversion of 99%" was confirmed, the reaction was terminated, and the time required for the reaction was compared.

The results are shown in the following Table 2. As in this Example where the amount of HCFC-123 was slightly lower than the critical value of 120 ppm, the necessary time to the end point of the reaction was "18 hours". As compared with that in Example 2 to be mentioned below, the reaction time herein was longer. However, as compared with that in Comparative Example 1 (26 hours) also to be mentioned below, it is understood that the reaction time was considerably shortened here.

TABLE 2

| Reaction Time | CG (%) | | | | |
|---|---|---|---|---|---|
| | HCFC-123 | TFIP | HFA | HFIP | PFIP |
| Before reaction | 0.0119 | 0.0000 | 99.73 | 0.0000 | — |
| 0.5 h | 0.0050 | 0.0028 | 82.10 | 17.84 | — |
| 1.0 h | 0.0013 | 0.0348 | 70.78 | 29.14 | — |
| 1.5 h | 0.0004 | 0.0400 | 65.63 | 34.27 | — |
| 2 h | 0.0000 | 0.0485 | 61.93 | 37.97 | — |
| 4 h | 0.0000 | 0.1314 | 37.54 | 62.20 | 0.0249 |
| 6 h | 0.0000 | 0.3144 | 20.67 | 78.88 | 0.0393 |
| 8 h | 0.0000 | 0.4832 | 13.20 | 86.22 | 0.0498 |
| 10 h | 0.0000 | 0.5596 | 7.99 | 91.40 | 0.0542 |
| 12 h | 0.0000 | 0.6275 | 4.54 | 94.76 | 0.0566 |
| 14 h | 0.0000 | 0.6619 | 2.61 | 96.66 | 0.0511 |
| 16 h | 0.0000 | 0.6933 | 1.63 | 97.61 | 0.0530 |
| 18 h | 0.0000 | 0.7544 | 0.95 | 98.23 | 0.0567 |

The crude HFIP obtained here was distilled under normal pressure, thereby collecting 2974 g of HFIP having a purity of 99.99% or more. At this time, the total yield was 95.0%.

Example 2

4.1 kg (18.63 mol) of hexafluoroacetone hydrate (trihydrate) [the composition of the hydrate and other impurities (including HCFC-123) are shown in Table 3 below, and the content of HCFC-123 before the start of the reaction was 7 ppm] was put into a 5-dm$^3$ stainless steel (SUS-316) autoclave equipped with a stirrer. Then, 0.195% by mass (% by mass relative to the HFA hydrate, and the same shall apply hereinafter) of 5%-Pd/alumina-supported catalyst (8 g), 0.122% by mass of 5%-Ru/alumina-supported catalyst (5 g), 0.122% by mass of aluminum hydroxide (5 g), and 0.0488% by mass of sodium hydrogencarbonate (0.2 g) were added thereto. The reactor was purged with hydrogen, and stirring was started with heating up to 95° C. with hot water while the hydrogen pressure was kept at 0.7 MPa. With this, hydrogen absorption began. After 8 hours, the reaction liquid was analyzed. With this, the HFA hydrate conversion was 95.45%. The GC purity of HFIP was 94.71%, TFA was 0.0039%, TFIP was 0.6800%, and HFA was 4.55%.

Subsequently, the reaction was continued while the reaction liquid was analyzed. At the time when the GC purity of HFA reached 1.00%, the heating and stirring were stopped to terminate the reaction. The reaction time up to this time (from the start to the end of the reaction) was 12 hours, and the HFA hydrate conversion was 99.00%. The GC purity of HFIP was 98.09%, TFIP was 0.7643%, and HFA was 1.00%.

The results are shown in the following Table 3. In the case where the amount of HCFC-123 contained in the HFA hydrate was 7 ppm, the "reaction rate lowering at the final stage of the reaction" was more noticeably prevented owing to the lowering of the content of HCFC-123, as compared with that in the above-mentioned Example 1. As a result, the reaction was finished within a short period of time of 12 hours. The results show that the case satisfying both the requirements that "the hydrogenation is started under a condition the content of HCFC-123 is not more than 120 ppm" and "an acid acceptor is made to be present in the system" realizes a special increase in the reaction rate.

TABLE 3

| Reaction Time | CG (%) | | | | |
|---|---|---|---|---|---|
| | HCFC-123 | TFIP | HFA | HFIP | PFIP |
| Before reaction | 0.0007 | 0.0000 | 99.80 | 0.0000 | — |
| 2 h | 0.0000 | 0.0795 | 36.81 | 43.05 | — |
| 4 h | 0.0000 | 0.3665 | 25.42 | 74.15 | 0.0364 |
| 6 h | 0.0000 | 0.5815 | 10.68 | 88.68 | 0.0500 |
| 8 h | 0.0000 | 0.6800 | 4.55 | 94.71 | 0.0550 |
| 10 h | 0.0000 | 0.7380 | 2.12 | 97.09 | 0.0572 |
| 12 h | 0.0000 | 0.7643 | 1.00 | 98.09 | 0.0528 |

The crude HFIP obtained here was subjected to a normal-pressure distillation, thereby recovering 2985 g of HFIP having a purity of 99.99%. At this time, the total yield was 95.35%.

Next, in the following [Example 3] to [Example 8], the reaction was terminated in 8 hours. Based on the GC purity (%) after the reaction, the effects in these Examples are compared with those in [Comparative Example 2] to [Comparative Example 3] to be mentioned below.

Example 3

200 g [(0.91 mol), containing 12 ppm of HCFC-123] of hexafluoroacetone hydrate (trihydrate) was put into a 0.5-dm$^3$ stainless steel (SUS-316) autoclave equipped with a stirrer. 0.2% by mass (% by mass relative to the HFA hydrate, and the same shall apply hereinafter) of 5%-Pd/alumina-supported catalyst (0.4 g) and 0.12% by mass of 5%-Ru/alumina-supported catalyst (0.24 g) were added thereto. The reactor was purged with hydrogen. With heating up to 95 to 99° C. in an oil bath, stirring was started while the hydrogen pressure was kept at 0.70 to 0.71 MPa. With this, hydrogen absorption began.

At the reaction time of 8 hours, the heating and stirring were stopped, and the reaction was terminated by cooling. The HFA hydrate conversion was 95.5%. Regarding the GC purity of the reaction liquid, TFIP was 0.366%, HFIP was 92.584%, PFIP was 0.108%, TeFIP was 0.040%, and HFA was 4.49%. The HFIP selectivity in this reaction was 99.4%.

Example 3 is an example of the hydrogenation in the absence of an acid acceptor. When compared with [Comparative Example 2] to [Comparative Example 3] to be mentioned below, it is understood that the case where the content of HCFC-123 in the hexafluoroacetone hydrate was 12 ppm realized an improved HFA hydrate conversion. In other words, it has been confirmed that, even though an acid acceptor is not added, "reaction rate lowering at the final stage of the reaction" can be prevented by reducing the content of HCFC-123.

Example 4

200 g [(0.91 mol), containing 12 ppm of HCFC-123] of hexafluoroacetone hydrate (trihydrate) was put into a 0.5-dm$^3$ stainless steel (SUS-316) autoclave equipped with a stirrer. 0.2% by mass (% by mass relative to the HFA hydrate, and the same shall apply hereinafter) of 5%-Pd/alumina-supported catalyst (0.4 g), 0.12% by mass of 5%-Ru/alumina-supported catalyst (0.24 g), 0.12% by mass of aluminum hydroxide (0.24 g) and 0.002% by mass of sodium hydrogencarbonate (0.004 g) were added thereto. The reactor was purged with hydrogen. With heating up to 94 to 97° C. in an oil bath, stirring was started while the hydrogen pressure was kept at 0.70 to 0.71 MPa. With this, hydrogen absorption began.

At the reaction time of 8 hours, the heating and stirring were stopped, and the reaction was terminated by cooling. The HFA hydrate conversion was 96.4%. Regarding the GC purity of the reaction liquid, TFIP was 0.573%, HFIP was 95.662%, PFIP was 0.140%, TeFIP was 0.066%, and HFA was 3.559%. The HFIP selectivity in this reaction was 99.2%.

As mentioned above, it is confirmed that the HFA hydrate conversion is extremely high as compared with those in [Comparative Example 2] to [Comparative Example 3] to be mentioned below.

This Example 4 differs from Example 3 in that an acid acceptor exists in the former. It is recognized that, owing to the presence of the acid acceptor, the reaction rate was increased more than in Example 3 (Needless-to-say, as compared with those in Examples 5 to 8, the HFA hydrate conversion herein is extremely high.). This strongly suggests that the "increased reaction rate" by addition of an acid acceptor and the "prevention of reaction rate lowering at the final stage of the reaction" by reducing the HCFC-123 content to 12 ppm are different and independent effects.

Example 5

200 g [(0.91 mol), containing 52 ppm of HCFC-123] of hexafluoroacetone hydrate (trihydrate) was put into a 0.5-dm$^3$ stainless steel (SUS-316) autoclave equipped with a stirrer. 0.2% by mass (% by mass relative to HFA hydrate, and the same shall apply hereinafter) of 5%-Pd/alumina-supported catalyst (0.4 g) and 0.12% by mass of 5%-Ru/alumina-supported catalyst (0.24 g) were added thereto. The reactor was purged with hydrogen. With heating up to 95 to 97° C. in an oil bath, stirring was started while the hydrogen pressure was kept at 0.70 to 0.71 MPa. With this, hydrogen absorption began.

At the reaction time of 8 hours, the heating and stirring were stopped, and the reaction was terminated by cooling. The HFA hydrate conversion was 93.6%. Regarding the GC purity of the reaction liquid, TFIP was 0.331%, HFIP was 93.061%, PFIP was 0.112%, TeFIP was 0.042%, and HFA was 6.449%. The HFIP selectivity in this reaction was 99.5%.

Example 6

197.52 g [(0.90 mol), containing 46 ppm of HCFC-123] of hexafluoroacetone hydrate (trihydrate) was put into a 0.5-dm$^3$ stainless steel (SUS-316) autoclave equipped with a stirrer. 0.2% by mass (% by mass relative to HFA hydrate, and the same shall apply hereinafter) of 5%-Pd/alumina-supported catalyst (0.4 g), 0.12% by mass of 5%-Ru/alumina-supported catalyst (0.24 g), 0.12% by mass of aluminum hydroxide (0.24 g) and 0.002% by mass of sodium hydrogencarbonate (0.004 g) were added thereto. The reactor was purged with hydrogen. With heating up to 94 to 98° C. in an oil bath, stirring was started while the hydrogen pressure was kept at 0.71 to 0.72 MPa. With this, hydrogen absorption began.

At the reaction time of 8 hours, the heating and stirring were stopped and the reaction was terminated by cooling. The HFA hydrate conversion was 94.6%. Regarding the GC purity of the reaction liquid, TFIP was 0.655%, HFIP was 93.775%, PFIP was 0.129%, TeFIP was 0.063%, and HFA was 5.378%. The HFIP selectivity in this reaction was 99.1%.

Example 7

200.02 g [(0.91 mol), containing 106 ppm of HCFC-123] of hexafluoroacetone hydrate (trihydrate) was put into a 0.5-dm$^3$ stainless steel (SUS-316) autoclave equipped with a stirrer. 0.2% by mass (% by mass relative to HFA hydrate, and the same shall apply hereinafter) of 5%-Pd/alumina-supported catalyst (0.4 g) and 0.12% by mass of 5%-Ru/alumina-supported catalyst (0.24 g) were added thereto. The reactor was purged with hydrogen. With heating up to 95 to 96° C. in an oil bath, stirring was started while the hydrogen pressure was kept at 0.70 to 0.71 MPa. With this, hydrogen absorption began.

At the reaction time of 8 hours, the heating and stirring were stopped, and the reaction was terminated by cooling. The HFA hydrate conversion was 91.9%. Regarding the GC purity of the reaction liquid, TFIP was 0.332%, HFIP was 91.420%, PFIP was 0.109%, TeFIP was 0.041%, and HFA was 8.097%. The HFIP selectivity in this reaction was 99.5%.

Example 8

200.02 g [(0.91 mol), containing 106 ppm of HCFC-123] of hexafluoroacetone hydrate (trihydrate) was put into a 0.5-dm$^3$ stainless steel (SUS-316) autoclave equipped with a stirrer. 0.2% by mass (% by mass relative to HFA hydrate, and the same shall apply hereinafter) of 5%-Pd/alumina-supported catalyst (0.4 g), 0.12% by mass of 5%-Ru/alumina-supported catalyst (0.24 g), 0.12% by mass of aluminum hydroxide (0.24 g) and 0.002% by mass of sodium hydrogencarbonate (0.004 g) were added thereto. The reactor was purged with hydrogen. With heating up to 95 to 97° C. with hot water, stirring was started while the hydrogen pressure was kept at 0.70 to 0.71 MPa. With this, hydrogen absorption began.

At the reaction time of 8 hours, the heating and stirring were stopped, and the reaction was terminated by cooling. The HFA hydrate conversion was 94.9%. Regarding the GC purity of the reaction liquid, TFIP was 0.515%, HFIP was 94.196%, PFIP was 0.126%, TeFIP was 0.057%, and HFA was 5.108%. The HFIP selectivity in this reaction was 99.3%.

As mentioned above, it is confirmed that the HFA hydrate conversion is high in [Example 3] to [Example 8] as compared with that in [Comparative Example 2] to [Comparative Example 3] to be mentioned below. When [Example 3] to [Example 4] are compared with [Example 5] to [Example 8], the HFA hydrate conversion in the former is higher than that in the latter. It is considered that, by employing the condition of "adding an acid acceptor" and "reducing the HCFC-123 content to a level not higher than a predetermined amount", and by reducing the amount of HCFC-123 to one falling within a more preferred range (5 ppm to 40 ppm), the reaction rate lowering at the final stage of the reaction can be effectively prevented.

Comparative Example 1

The same operation as in Example 1 was carried out under the same condition therein, except that as the starting material an HFA hydrate (trihydrate) having a HCFC-123 content of 144 ppm was used and that 0.2 g of sodium hydrogencarbonate was added to the reaction system.

The reaction was carried out while the reaction liquid was analyzed. At the time when the GC purity of HFA reached 1.00% (reaction conversion=99%), the heating and stirring were stopped, and the reaction was terminated by cooling. Up to this time, the reaction time (from the start to the end of reaction) was 26 hours. Although the other conditions than the amount of HCFC-123 were the same as those in Examples 1 and 2, the reaction time was considerably long in Comparative Example 1. Regarding the GC purity, HFIP was 98.38%, TFIP was 0.5473%, and HFA was 1.00%.

The results are shown in Table 4 below. As mentioned above, it is understood that, even in a case where an acid acceptor is added, when the amount of HCFC-123 is more than 120 ppm, the reaction time is longer than those in Example 1 and Example 2. This means that the "reaction rate lowering at the final stage of the reaction" is not correlated to "addition of an acid acceptor in the hydrogenation" but depends on the content of HCFC-123.

TABLE 4

| Reaction Time | CG (%) | | | | |
| --- | --- | --- | --- | --- | --- |
| | HCFC-123 | TFIP | HFA | HFIP | PFIP |
| Before reaction | 0.0144 | 0.0000 | 99.69 | 0.0000 | — |
| 0.5 h | 0.0042 | 0.0156 | 80.40 | 19.56 | — |
| 1.0 h | 0.0013 | 0.0205 | 69.29 | 30.66 | — |
| 1.5 h | 0.0006 | 0.0254 | 61.30 | 38.63 | — |
| 2 h | 0.0000 | 0.0324 | 56.99 | 42.92 | 0.0131 |
| 4 h | 0.0000 | 0.0941 | 33.53 | 66.26 | 0.0389 |
| 6 h | 0.0000 | 0.1668 | 22.36 | 77.36 | 0.0492 |
| 8 h | 0.0000 | 0.2670 | 14.22 | 85.39 | 0.0623 |
| 10 h | 0.0000 | 0.3504 | 9.35 | 90.19 | 0.0673 |
| 12 h | 0.0000 | 0.4133 | 6.42 | 93.06 | 0.0712 |
| 14 h | 0.0000 | 0.4239 | 3.95 | 95.55 | 0.0561 |
| 16 h | 0.0000 | 0.4647 | 2.62 | 96.84 | 0.0565 |
| 18 h | 0.0000 | 0.4938 | 1.93 | 97.51 | 0.0585 |
| 20 h | 0.0000 | 0.5365 | 1.45 | 97.94 | 0.0663 |
| 26 h | 0.0000 | 0.5473 | 1.00 | 98.38 | 0.0652 |

Next, in the following Comparative Example 2 and Comparative Example 3, the reaction was terminated in 8 hours, like in the above-mentioned Example 3 to Example 8, and the effects were compared based on the GC purity (%) after the reaction.

Comparative Example 2

200 g [(0.91 mol), containing 130 ppm of HCFC-123] of hexafluoroacetone hydrate (trihydrate) was put into a 0.5-dm$^3$ stainless steel (SUS-316) autoclave equipped with a stirrer. 0.2% by mass (% by mass relative to HFA hydrate, and the same shall apply hereinafter) of 5%-Pd/alumina-supported catalyst (0.4 g) and 0.12% by mass of 5%-Ru/alumina-supported catalyst (0.24 g) were added thereto. The reactor was purged with hydrogen. With heating up to 96° C. in an oil bath, stirring was started while the hydrogen pressure was kept at 0.7 MPa. With this, hydrogen absorption began.

At the reaction time of 8 hours, the heating and stirring were stopped, and the reaction was terminated by cooling. The HFA hydrate conversion was 86.78%. Regarding the GC purity of the reaction liquid, TFIP was 0.285%, HFIP was 86.30%, and HFA was 13.22%.

As mentioned above, it is understood that, when the content of HCFC-123 is 130 ppm, the HFA hydrate conversion in the GC purity of the reaction liquid after the reaction time of 8 hours is lower than those in Example 3 to Example 8. This suggests that, irrespective of "addition of an acid acceptor in the hydrogenation", the reaction rate lowers at the final stage of the reaction when the content of HCFC-123 is more than 120 ppm.

Comparative Example 3

196.55 g [(0.91 mol), containing 198 ppm of HCFC-123] of hexafluoroacetone hydrate (trihydrate) was put into a 0.5-dm$^3$ stainless steel (SUS-316) autoclave equipped with a stirrer. 0.2% by mass (% by mass relative to HFA hydrate, and the same shall apply hereinafter) of 5%-Pd/alumina-supported catalyst (0.4 g), 0.12% by mass of 5%-Ru/alumina-supported catalyst (0.24 g), 0.12% by mass of aluminum hydroxide (0.24 g) and 0.002% by mass of sodium hydrogencarbonate (0.004 g) were added thereto. The reactor was purged with hydrogen. With heating up to 93 to 96° C. in an oil bath, stirring this was started while the hydrogen pressure was kept at 0.7 MPa. With this, hydrogen absorption began.

At the reaction time of 8 hours, the heating and stirring were stopped, and the reaction was terminated by cooling. The HFA hydrate conversion was 84.50%. Regarding the GC purity of the reaction liquid, TFIP was 0.505%, HFIP was 83.85%, and HFA was 15.50%.

As mentioned above, it is understood that, when the content of HCFC-123 is 198 ppm, the HFA hydrate conversion in the GC purity of the reaction liquid after the reaction time of 8 hours is lower than those in Example 3 to Example 8 even though an acid acceptor is added. This suggests that, when the content of HCFC-123 far exceeds 120 ppm, the reaction rate lowers more at the final stage of the reaction.

[Reference Example] Production of Hexafluoroacetone Trihydrate (an Example of Purification by Simple Distillation of Crude Hexafluoroacetone Trihydrate)

200 g (0.91 mol) of the crude hexafluoroacetone trihydrate produced in the above-mentioned Preparation Example was put into a 0.5-dm$^3$ stainless steel (SUS-316) autoclave equipped with a stirrer. In a simple distillation apparatus attached thereto, a simple distillation was conducted under a pressure of 0.05 MPa and at an internal temperature of 70° C. to 75° C.

As a result, 170 g of a distillate of hexafluoroacetone trihydrate was obtained. The resultant distillate was analyzed for quantification of the fluoride ions therein through gas chromatography. With this, the amount of HCFC-123 contained in the hexafluoroacetone trihydrate was 1504 ppm.

As above, it is understood that, even if a simple distillation is conducted after synthesis of the hexafluoroacetone hydrate, the content of HCFC-123 could not be lower than 120 ppm.

Example 9

14.13 g (0.42 mol) of 95% paraformaldehyde, 132.4 g (1.35 mol) of 97% sulfuric acid, 53.02 g (2.65 mol) of hydrogen fluoride and 43.69 g (0.26 mol) of hexafluoroisopropanol obtained in Example 1 were put into a reactor having a trap cooled at −15° C. or so connected thereto. Stirring was conducted at 20° C. for 2 to 3 hours. Subsequently, this was heated for 5 to 6 hours so as to be finally at 65° C. to 75° C., while stirring was continued. During this, with stirring, the product in the reactor gradually distilled out. Therefore, the product was collected in the trap outside of the system.

At the time when no more distillate formed, the reaction was stopped. The trap in which the product was collected (an organic phase containing fluoromethyl hexafluoroisopropyl ether) was washed with water, then an acid aqueous solution and then a basic aqueous solution to give a two-layer mixed liquid of an aqueous layer containing the unreacted hexafluoroisopropanol and hydrogen fluoride, and an organic layer containing fluoromethyl hexafluoroisopropyl ether. Subsequently, the aqueous layer containing 1,1,1,3,3,3-hexafluoroisopropanol was separated and removed from the mixed liquid. The organic layer containing fluoromethyl hexafluoroisopropyl ether was subjected to a distillation to give 34 g (0.17 mol) of fluoromethyl hexafluoroisopropyl ether having a purity of more than 99%, in an yield of 65.06%. The HFIP conversion was 72.51%.

INDUSTRIAL APPLICABILITY

Hexafluoroisopropanol that is the target compound of the present invention can be used as an intermediate of medicines and agricultural chemicals and as a solvent for analysis and as a washing solvent for electronic materials, etc. Sevoflurane derived from hexafluoroisopropanol can be used as a medicinal chemical such as an inhalation anesthetic, etc.

The invention claimed is:

1. A method for producing a fluoromethyl hexafluoroisopropyl ether (sevoflurane), comprising the steps of:
   (a) purifying a mixture containing hexafluoroacetone and greater than 120 ppm of 1,1,1-trifluoro-2,2-dichloroethane as an impurity, thereby obtaining a purified hexafluoroacetone containing 5-120 ppm of the 1,1,1-trifluoro-2,2-dichloroethane;
   (b) bringing hydrogen ($H_2$) into contact with the purified hexafluoroacetone in the presence of a catalyst, thereby hydrogenating the hexafluoroacetone into a hexafluoroisopropanol; and
   (c) reacting the hexafluoroisopropanol, formaldehyde, and hydrogen fluoride in the presence of a Lewis acid or a Broensted acid.

2. The method as claimed in claim 1, wherein the step (a) is conducted by a distillation.

3. The method as claimed in claim 1, the step (a) comprises the steps of:
   (d) bringing water into contact with the mixture containing hexafluoroacetone and greater than 120 ppm of 1,1,1-trifluoro-2,2-dichloroethane as an impurity, thereby converting the hexafluoroacetone contained in the mixture into hexafluoroacetone trihydrate; and
   (e) distilling a mixture obtained by the step (d).

4. The method as claimed in claim 3, wherein the step (e) comprises the steps of:
   (f) supplying the mixture obtained by the step (d) into a rectifying column; and
   (g) conducting the distillation with a number of theoretical plates of from 2 to 50 and a reflux ratio of 0.5-8.0.

5. The method as claimed in claim 1, wherein the step (a) comprises the step of:
   (h) conducting a quantitative analysis of the hexafluoroacetone by gas chromatography during the purification to see if the content of the 1,1,1-trifluoro-2,2-dichloroethane in the mixture is 5-120 ppm.

6. The method as claimed in claim 1, wherein the catalyst used in the step (b) is a first catalyst comprising at least one metal selected from the group consisting of palladium, platinum, ruthenium, rhodium, and nickel, or a second catalyst comprising the at least one metal supported on a carrier.

7. The method as claimed in claim 1, wherein the catalyst used in the step (b) is at least one selected from the group consisting of a third catalyst comprising palladium and ruthenium that are supported on the same carrier, and a fourth catalyst comprising a mixture of a catalyst containing palladium supported on a carrier and a catalyst containing ruthenium supported on a carrier.

8. The method as claimed in claim 1, wherein the hydrogenation of the step (b) is conducted in the presence of an acid acceptor in a reaction system.

9. The method as claimed in claim 8, wherein a carbonate or hydrogencarbonate of an alkali metal and a hydroxide of a metal of group 13 of the periodic table are used together as the acid acceptor in the step (b).

10. The method as claimed in claim 1, wherein the mixture containing hexafluoroacetone and greater than 120 ppm of 1,1,1-trifluoro-2,2-dichloroethane as an impurity to be purified by the step (a) is prepared by a method comprising the steps of:
   (i) chlorinating acetone by chlorine ($Cl_2$), thereby obtaining a mixture containing hexachloroacetone; and
   (j) fluorinating the hexachloroacetone by bringing hydrogen fluoride into contact with the mixture obtained by the step (i), thereby preparing the mixture containing hexafluoroacetone and greater than 120 ppm of 1,1,1-trifluoro-2,2-dichloroethane as an impurity.

11. The method as claimed in claim 1, wherein the hexafluoroisopropanol produced by the step (b) is separated by a method comprising the steps of:
   (k) separating the catalyst of the step (b) from a reaction mixture obtained by the step (b), thereby obtaining a liquid component; and
   (l) distilling the liquid component, thereby separating the hexafluoroisopropanol.

12. A method for producing a fluoromethyl hexafluoroisopropyl ether (sevoflurane), comprising the steps of:
   (m) chlorinating acetone by chlorine ($Cl_2$), thereby obtaining a mixture containing hexachloroacetone;
   (n) fluorinating the hexachloroacetone by bringing hydrogen fluoride into contact with the mixture obtained by the step (m), thereby preparing a mixture containing hexafluoroacetone and greater than 120 ppm of 1,1,1-trifluoro-2,2-dichloroethane as an impurity;
   (o) bringing water into contact with the mixture prepared by the step (n), thereby converting the hexafluoroacetone contained in the mixture into hexafluoroacetone trihydrate;
   (p) supplying a mixture obtained by the step (o) into a rectifying column;
   (q) conducting a distillation of the mixture obtained by the step (o) in the rectifying column with a number of theoretical plates of from 2 to 50 and a reflux ratio of 0.5-8.0 until the content of the 1,1,1-trifluoro-2,2-dichloroethane in the mixture becomes 5-120 ppm, thereby obtaining a purified hexafluoroacetone trihydrate containing 5-120 ppm of the 1,1,1-trifluoro-2,2-dichloroethane;
   (r) bringing hydrogen ($H_2$) into contact with the purified hexafluoroacetone trihydrate in the presence of an acid acceptor and in the presence of at least one catalyst selected from the group consisting of a first catalyst comprising palladium and ruthenium that are supported on the same carrier and a second catalyst comprising a mixture of a catalyst containing palladium supported on a carrier and a catalyst containing ruthenium supported on a carrier, thereby producing a hexafluoroisopropanol; and (s) reacting the hexafluoroisopropanol obtained by the step (r) with formaldehyde and hydrogen fluoride in the presence of a Lewis acid or a Broensted acid, thereby producing the fluoromethyl hexafluoroisopropyl ether (sevoflurane).

* * * * *